United States Patent [19]

Hirschmann, Jr.

[11] 4,027,342

[45] June 7, 1977

[54] GOGGLE VENTILATOR

[75] Inventor: Jack B. Hirschmann, Jr., Buzzards Bay, Mass.

[73] Assignee: H. L. Bouton, Company, Inc., Buzzards Bay, Mass.

[22] Filed: July 9, 1975

[21] Appl. No.: 594,610

[52] U.S. Cl. .................................................. 2/436
[51] Int. Cl.² .......................................... A61F 9/02
[58] Field of Search ................. 2/14 N, 14 K, 14 R, 2/9, 10, 436, 437

[56] References Cited

UNITED STATES PATENTS

| 2,877,463 | 3/1959 | Watkins | 2/14 N |
| 3,000,011 | 9/1961 | Sterne et al. | 2/14 N |
| 3,141,172 | 7/1964 | Hirschmann | 2/14 N |
| 3,418,658 | 12/1968 | Danico | 2/14 N |

Primary Examiner—Werner H. Schroeder
Assistant Examiner—Peter Nerbun
Attorney, Agent, or Firm—Biebel, French & Nauman

[57] ABSTRACT

A two-part goggle ventilator includes a pin on one part and a pin receiving opening in the other part providing for quick, convenient and reliable attachment of the ventilator in a complementary aperture in a goggle. When assembled on the goggle, the ventilator allows air to flow through the goggle but provides high resistance to intrusion of liquids and other foreign matter.

8 Claims, 5 Drawing Figures

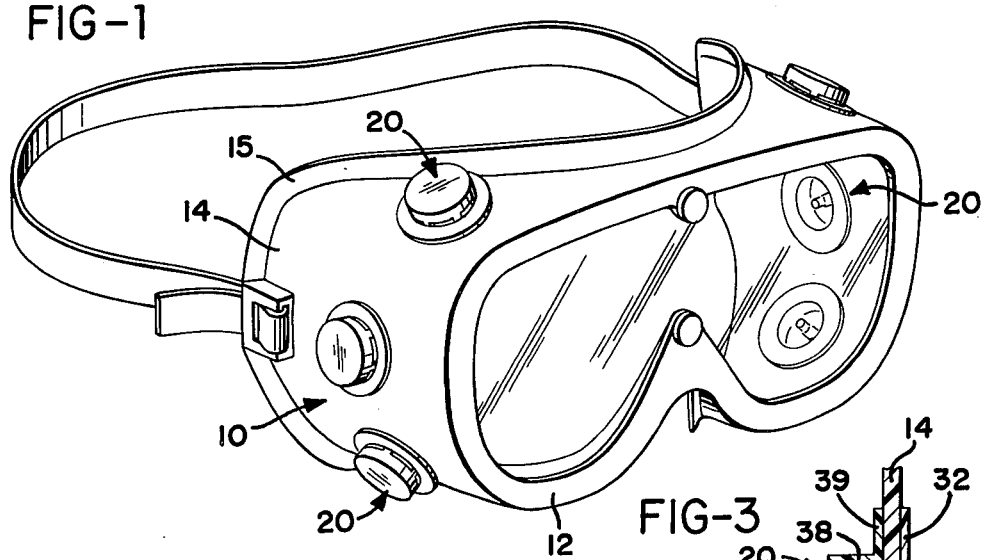
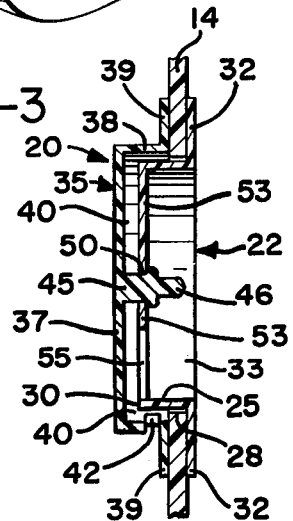
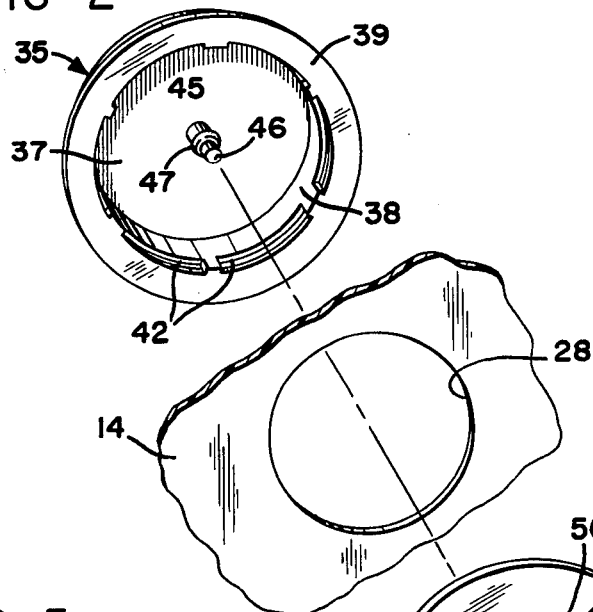
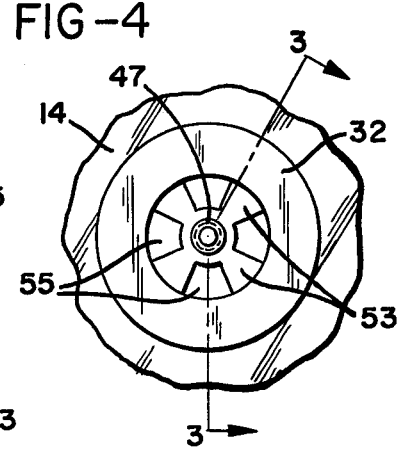
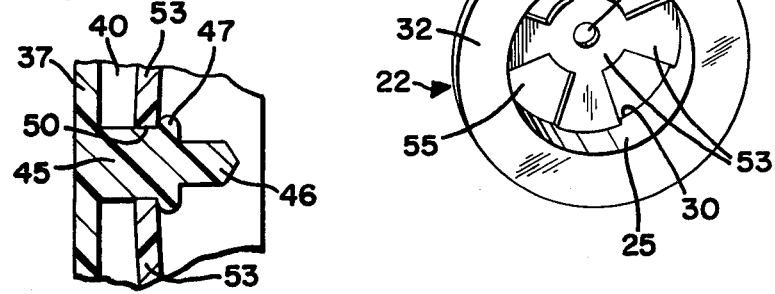

GOGGLE VENTILATOR

BACKGROUND OF THE INVENTION

This invention relates to goggle ventilators, and more particularly to improvements in ventilators such as shown in U.S. Pat. No. 3,141,172, issued to the assignee of the present invention.

The goggle ventilator illustrated in the above patent provides an inexpensive and effective means for ventilating the space within a goggle while preventing the intrusion of foreign matter and liquids. A narrow, circuitous air passage within the ventilator blocks the direct movement of solids through the ventilator, and liquids are excluded by capillary action within the narrow ventilator passage. The ventilator is formed in two parts which can be fastened onto the goggle either by threading an inner member into an outer member, or by cementing one to the other or to the goggle frame.

SUMMARY OF THE INVENTION

Briefly, the present invention provides an improved means for clamping a two-part ventilator onto a safety goggle. With the present invention, one of the ventilator parts, such as an inner tubular portion, is provided with an opening which receives a pin therethrough from the other ventilator part. The pin is held in the opening in friction-tight relation to hold the ventilator parts together. Since the ventilator parts are provided with complementary goggle-engaging flanges, the ventilator is quickly and permanently clamped onto the goggle by assembling the ventilator through a properly sized ventilation aperture in the goggle frame.

The present invention thus has several advantages, foremost being the ease and speed with which the ventilator may be assembled onto a goggle. Previously, it has been necessary to thread or cement the ventilator portions into place. As will be appreciated, this can be messy and time-consuming, and may require additional equipment and/or personnel. Further, prior art methods of attachment leave little latitude for adjusting the clamping force, since the ventilator must always be clamped tightly or cemented permanently, to assure a satisfactory seal and to be sure that if it has been threaded on, it will not loosen.

In the present invention, the pin receiving opening is carried on a resilient perforated web across one end of the inner tubular member. This web is ordinarily spaced slightly from the base of the pin in the other ventilator portion to provide latitude in the precise axial position at which the pin is gripped by the opening in the web. Thus, for example, the pin may be driven a little "too far" through the opening and the web will then act as a spring to place a constant clamping force on the ventilator flanges as they clamp the side wall of the goggle.

As indicated, the present invention simplifies and expedites assembly of the ventilator onto the goggle. There is no need to locate and engage threaded members or to delay while cement or solvents are being applied and allowed to set. Rather, the ventilator parts are assembled simply by pressing them together in position on the goggle. Also, due to the smooth and uncomplicated configurations of the two ventilator parts, they are well suited for inexpensive mass production by injection molding.

It is therefore an object of the present invention to provide improved means for securing a goggle ventilator onto a goggle; a ventilator securing means which provides for controlling the clamping force of the ventilator on the goggle; which provides for fast, convenient, and inexpensive assembly; which includes a pin on one part of the ventilator which is received in friction-tight relation in a pin receiving opening carried in the other part of the ventilator; and to accomplish these objects and purposes in a durable and reliable configuration readily suited to inexpensive mass production and assembly.

Other objects and advantages of the invention will be apparent from the following description, the accompanying drawings and the appended claims.

BRIEF DESCRIPTION OF THE DRAWINGS

FIG. 1 is a perspective view of a ventilated goggle incorporating ventilators constructed in accordance with the present invention;

FIG. 2 is an exploded perspective view of the component parts of one of the ventilators in the FIG. 1 goggle;

FIG. 3 is a section through one of the ventilators taken generally on line 3—3 of FIG. 4;

FIG. 4 is a view of one of the ventilators assembled onto the goggle, looking from inside the goggle outward through the ventilator; and FIG. 5 is an enlarged fragment of FIG. 3.

DESCRIPTION OF THE PREFERRED EMBODIMENT

FIG. 1 illustrates a ventilated safety goggle similar to the goggle illustrated in U.S. Pat. No. 3,141,172. As described therein, the goggle includes a frame 10 having a rim portion 12 which encloses the periphery of the lens 13, and a back portion or wall 14 extending rearwardly from the rim and terminating in a flange 15 for engaging the face of the wearer.

The ventilators 20, which are preferably identical in construction and located on opposite sides of frame 10, are shown in detail in FIGS. 2–4. Each ventilator 20 includes a generally cup-shaped inner part 22 having a hollow tubular portion 25 adapted for insertion through a suitably sized ventilator aperture 28 formed in the goggle wall 14. The inner part 22 is inserted into the aperture 28 from inside the goggle, and when so inserted, the outer end 30 of the tubular portion 25 extends outwardly and is spaced from the wall 14. An integral annular flange 32 on the end of the tubular portion 25 inside the goggle and opposite end 30 is sized to engage the inner surface of the goggle wall 14, and when clamped firmly thereon is in sealing engagement with the wall. The inner part 22 thus provides a ventilating opening or air passage 33 connecting axially through the tubular portion 25 from outside the wall 14 into the interior of the goggle.

Ventilator 20 also includes a generally cup-shaped cap part 35 having an impervious outer end 37, a cylindrical body portion 38, and a peripheral flange 39. Body portion 38 is arranged to be assembled on the goggle in telescoping relation with tubular portion 25, portion 38 providing axially inwardly extending sides which overlap the outer end 30 of the tubular portion 25. As may be seen in FIG. 3, portion 38 is proportioned to stand in spaced relation to the sides and outer end of tubular portion 25 to provide a ventilating space or passageway 40 between ventilator openings 42 formed through portion 38 and opening 33 which passes through the center of tubular portion 25. Openings 42 are located adjacent flange 39 and axially inwardly of the radial projection of the outer end 30 of the tubular portion 25. In these respects, therefore, the ventilator of the present invention is similar to that in the above-noted U.S. Pat. No. 3,141,172, and similarly provides good ventilation for the goggles while protecting against intrusion of foreign solids and liquids.

In order to hold the ventilators 20 on the goggle, each ventilator cap part 35 includes a pin 45 extending axially inwardly thereof from the end wall 37 and including a pilot portion 46 of reduced diameter and a peripheral rib or bead 47 of greater diameter than the inner end portion of the pin. In the assembled device, the pin 45 is received through a pin-receiving opening 50 in a web 53 which forms the end wall across the outer end 30 of the inner member tubular portion 25. Web 53 includes several perforations 55 which connect the axial ventilating opening 33 with the ventilating passageway 40 on the other side thereof.

As illustrated in FIGS. 2 and 3, the ventilator 20 is assembled quite easily onto the goggle wall 14 simply by inserting the inner member tubular portion 25 outwardly through the ventilation aperture 28 in wall 14, and then forcing the cap pin 45 through the inner member pin-receiving opening 50 until the bead 47 passes through the opening to seat on the surrounding surface portion of the web 53. Pin 45 is then firmly held in interlocked relation to prevent the ventilator portions 22 and 35 from separating.

As shown in FIGS. 3 and 5, the web portion 53 acts somewhat as a spring since it is resiliently displaceable in the axial direction. Thus the force with which the ventilator flanges 32 and 39 grip the goggle wall 14 may be controlled by the degree to which pin 45 is forced through opening 50. It is thus easy to establish a permanent tension between these members to seal the ventilator flanges onto the goggle wall.

As may be seen, therefore, the present invention provides numerous advantages. The ventilators may be assembled onto the goggle in minimum time and with minimum effort. The simplicity of their individual portions lends them readily to inexpensive mass production by injection molding. Once assembled, the ventilators remain permanently affixed and provide a firm, liquid-tight seal between the ventilator flanges 32 and 39 and the goggle wall 14.

The present invention also lends itself to suitable modification where desired. For example, pin 45 might be proportioned or have a textured surface to enhance its frictional engagement within opening 50, or vice versa, or the pilot end 46 of the pin opposite the outer end 37 of cap part 35 could be melted after the ventilator is assembled onto the goggle to enlarge the pin end 46. The latter would prevent subsequent withdrawal of the pin through the pin receiving opening 50. It should also be appreciated that a plurality of pins and pin-receiving openings may be used, and the pin or pins, and their openings, need not lie right on the ventilator axis.

While the form of apparatus herein described constitutes a preferred embodiment of this invention, it is to be understood that the invention is not limited to this precise form of apparatus, and that changes may be made therein without departing from the scope of the invention.

What is claimed is:

1. A goggle ventilator for use in a safety goggle frame including an impervious wall having at least one aperture therethrough for receiving the ventilator, said ventilator including an inner part having an air passage therethrough and a separate outer part, both of said parts being cup-shaped and each including a tubular side wall and an end wall, means forming a pair of axially spaced inner and outer annular flanges mounted, respectively, on said inner and outer ventilator parts, said flanges being received one each on each side of the goggle wall at said aperture to support said inner and outer parts directly on the goggle wall in sealing relation with the wall and with said end walls of said parts in generally parallel and aligned relation, and means in said outer part defining at least one ventilating opening therethrough for providing an air passage connecting through the inner part air passage into the interior of the goggle, improved means for securing said ventilator inner and outer parts together, comprising:
   a. a solid pin on said end wall of one of said ventilator parts,
   b. means including a pin-receiving opening in said end wall of the other of said ventilator parts dimensioned to receive and hold said pin therethrough in interlocked relation to hold said ventilator parts together, said pin and pin-receiving opening providing for ready assembly of said ventilator onto the goggle with said ventilator flanges clamped firmly thereon and providing resistance against separation of said ventilator inner and outer parts,
   c. said parts being proportioned to position said end walls thereof in spaced relation in the assembled position of said ventilator, and
   d. one of said end walls being resilient to act as a spring maintaining said flanges in clamping relation with the goggle wall with a force controlled by the degree to which said pin is inserted through said pin-receiving opening.

2. The device of claim 1 wherein said pin and pin-receiving opening are substantially co-axial with said ventilator inner and outer parts.

3. The device of claim 1 wherein said pin is mounted on said ventilator outer part, and said pin-receiving opening is provided in said inner part of said ventilator.

4. The device of claim 3 further comprising a resilient, perforated web mounted on said inner ventilator part, said pin-receiving opening being formed in said web, said web being spaced slightly from the base of said pin when the ventilator parts are assembled onto the goggle to cause said web to act as a spring for clamping the ventilator flanges onto the goggle with a force controlled by the degree to which said pin is inserted through said pin-receiving opening, and said perforations in said web connecting said air passage between said ventilator outer part and said air passage through said inner ventilator part.

5. The device of claim 1 wherein said pin is of different diameters at various points along the axis thereof to improve the engagement thereof in said pin receiving opening.

6. The device of claim 1 wherein said pin includes a peripheral bead located and proportioned to interlock with the outer surfaces of said other ventilator part after passage through said pin-receiving opening.

7. In a goggle ventilator for use in a safety goggle frame including an impervious wall having at least one aperture therethrough for receiving said ventilator, said ventilator including a hollow inner tubular part and a separate outer cap part, said tubular part extending axially through said aperture and terminating at one end interiorly of said goggle frame and at an outer end exteriorly of said goggle wall with the outer end positioned in spaced relation from said wall, means forming a pair of axially spaced inner and outer annular flanges on said ventilator tubular and cap parts respectively, said flanges being received one each on each side of said goggle wall at said aperture to support said tubular and cap parts directly on said goggle wall in sealing relation therewith, said ventilator cap part having an impervious outer end and axially inwardly extending sides overlapping the outer end of said tubular part with the inner surfaces of said cap being proportioned respectively in spaced relation to the sides and outer end of said tubular part, and means in said cap sides defining at least one ventilating opening therethrough positioned adjacent said outer flange and axially inwardly of the radial projection of the outer end of said tubular part for connecting through said tubular part into the interior of said goggle, improved means for securing said ventilator tubular and cap parts together, comprising:

a. a solid pin mounted substantially co-axially on said ventilator cap part, b. a resilient, perforated web on said tubular part of said ventilator substantially in a radial plane near the outer end thereof, said perforations in said web connecting said ventilator cap part and the interior of said tubular part, c. means including a pin-receiving opening formed substantially co-axially in said perforated web for receiving said pin therethrough in friction-tight relation to hold said ventilator parts together, and d. said web being spaced slightly from the base of said pin when the ventilator parts are assemled onto the goggle to cause said web to act as a spring for clamping the ventilator flanges onto the goggle with a force controlled by the degree to which said pin is inserted through said pin-receiving opening, said pin and pin-receiving opening providing for ready assembly of said ventilator onto said goggle with said ventilator flanges clamped firmly thereon and providing frictional resistance against separation of said ventilator tubular and cap parts.

8. The device of claim 6 further comprising a pilot portion of reduced diameter on the end of said pin opposite said one ventilator part and extending outwardly beyond said bead.

* * * * *